United States Patent [19]

Tsuchida

[11] Patent Number: 5,258,929
[45] Date of Patent: Nov. 2, 1993

[54] METHOD FOR MEASURING THERMAL CONDUCTIVITY

[75] Inventor: Yoshiki Tsuchida, Tama, Japan

[73] Assignee: Ishikawajima-Harima Heavy Industries Co., Ltd., Tokyo, Japan

[21] Appl. No.: 795,308

[22] Filed: Nov. 21, 1991

Related U.S. Application Data

[63] Continuation of Ser. No. 298,010, Jan. 18, 1989, abandoned.

[30] Foreign Application Priority Data

Jan. 18, 1988 [JP] Japan ................................. 63-7801
Jan. 18, 1988 [JP] Japan ................................. 63-7802
Sep. 21, 1988 [JP] Japan ............................. 63-236727

[51] Int. Cl.$^5$ ............................................. G01N 25/18
[52] U.S. Cl. ...................................... 364/557; 374/44
[58] Field of Search ............... 364/557; 374/43, 44

[56] References Cited

U.S. PATENT DOCUMENTS

| | | | |
|---|---|---|---|
| 3,263,485 | 8/1966 | Mahmoodi | 374/44 |
| 3,733,887 | 5/1973 | Stanley et al. | 374/44 |
| 3,892,125 | 7/1975 | Nunogaki | 374/43 |
| 4,259,859 | 4/1981 | Iida et al. | 374/43 |
| 4,568,198 | 2/1986 | Szabó et al. | 364/557 X |
| 4,630,938 | 12/1986 | Piórkowska-Palczewska et al. | 374/43 X |
| 4,852,027 | 7/1989 | Bowman et al. | 364/557 |
| 5,099,441 | 3/1992 | Mazzio | 364/557 |

FOREIGN PATENT DOCUMENTS

| | | | |
|---|---|---|---|
| 0741126 | 6/1980 | U.S.S.R. | 374/43 |
| 1096549 | 6/1984 | U.S.S.R. | 374/43 |
| 1163232 | 6/1985 | U.S.S.R. | 374/44 |

OTHER PUBLICATIONS

Lindelourg; Engineer in Training Review Manual; 6th Ed ©1982; pp. 15–16 to 15–17.

Taylor et al. "Direct Heating Methods for Measuring Thermal Conductivity of Solids at High Temperatures", High Temp.–High Pres., vol. 1, No. 6, pp. 663–673, 1969.

Keiji Naito et al., Measurement of Theremal Conductivity and Diffusivity by Means of Scanning Temperature Method, Journal of Nuclear Science and Technology, vol. 13, No. 9, Sep. 1976, pp. 508–516.

1989 Annual Book of ASTM Standards; Section 14; vol. 14.01; pp. 1–12.

*Primary Examiner*—Thomas G. Black
*Assistant Examiner*—Michael Zanelli
*Attorney, Agent, or Firm*—Oblon, Spivak, McClelland, Maier & Neustadt

[57] ABSTRACT

The present invention provides a method for measuring thermal conductivity of a material at a stationary state at an elevated temperature T. The method is essentially composed of the steps of: (a) preparing a specimen of the material having first and second surfaces parallel to each other, thickness defined by the first and the second surfaces being constant, a sectional area parallel to the first and the second surfaces of the specimen being constant through the specimen; (b) measuring heat flows Q1 to QN through the specimen at thermally stationary states S1 to SN wherein the temperature of the first surface of the specimen is To which is far lower than the temperature T and the temperature of the second surface of the specimen is T1 to TN which are in the vicinity of the temperature T, T1 to TN corresponding to the states S1 to SN; and (c) calculating the thermal conductivity of the specimen on the basis of the thickness and sectional area, temperatures of the first and the second surfaces, and heat flows through the specimen.

14 Claims, 7 Drawing Sheets

METHOD FOR MEASURING THERMAL CONDUCTIVITY

This is a continuation of application Ser. No. 07/298,010, filed on Jan. 18, 1989, now abandoned.

BACKGROUND OF THE INVENTION

This invention relates to a measurement method for thermal conductivity under steady state conditions at high temperatures which can be appropriately applied to various kinds of materials such as heat insulating materials.

In general, the thermal conductivity of insulating materials varies depending on the temperature. As shown in FIG. 14, it is a general characteristic that the higher the temperature, the higher the heat conductivity. In other words, heat is more easily conducted through a material at a high temperature than at a lower temperature. For heat insulating materials to be used at over 1,000° C., it is necessary to test them at the temperatures at which they will be used.

A conventional method for measurement of thermal conductivity is described in ASTM C177-85 etc., for example, as shown in FIG. 15. A conventional apparatus for measuring thermal conductivity consists of a main heater b and an auxiliary heater c which are disposed respectively in the upper and lower parts of the enclosure a and are designed to generate a downward steady heat flow. A heat flow meter d is disposed above the auxiliary heater c and is used to measure the steady heat flow.

When thermal conductivity is measured with this conventional apparatus, a specimen S is first placed at the center of the enclosure a, and standard heat transfer plates S1 and S2 of known thermal conductivity are positioned on and under the specimen S. Second, the main heater b and the auxiliary heater c are controlled to create a steady state heat flow in the enclosure. The average temperature of specimen S is maintained at the temperature T° C. at which the heat conductivity is to be measured whereas the temperature within the specimen varies as shown in FIG. 15.

Next, the steady state temperatures of the upper and lower surfaces of the specimen S are accurately measured with thermometers e. The thermal conductivity of the specimen S at temperature T° C. (the average temperature of specimen S) can then be calculated from the temperature difference between the upper and lower surfaces of the specimen S and the value of the steady state heat flow which is measured by a heat flow meter d.

The following equation relates the heat flow Q (Kcal/h) at a state where the temperatures at the upper and lower surfaces of specimen S are, $\theta_1$ and $\theta_2$ respectively, the $$Q = (\lambda/\tau) \cdot A (\theta_1 - \theta_2)$$

From this formula, the following equation can be obtained:

$$\lambda = Q \cdot \tau / A (\theta_1 - \theta_2) \quad (1)$$

The standard heat transfer plates S1 and S2 in the above mentioned conventional thermal conductivity measurement apparatus are designed to keep the specimen S at a high temperature as well as to compare the thermal conductivity of the specimen with the known thermal conductivity of the standard heat transfer plates S1 and S2. This thermal conductivity can be obtained from the surface temperatures which are measured by thermometers f, and heat flow Q.

Heaters g for compensating the temperature of the inner surface of the enclosure 'a' maintain the surface temperature as shown by the line B in FIG. 15. Thus, the heat transfer between enclosure 'a' and its internal space is suppressed. This arrangement is for the purpose of preventing the heat flow through the peripheral part of the enclosure.

It is rather difficult or impossible at higher temperatures to conduct accurate measurement of thermal conductivity of a specimen with the conventional measuring apparatus since its surfaces are in contact with the standard heat transfer plates and thermocouples are used for temperature measuring. This limits the temperature at which the apparatus can be used.

It is possible to remove the upper standard heat transfer plate, but the lower standard heat transfer plate cannot be removed because the plate is indispensable in keeping the heat flow meter d at a lower temperature when the measuring temperature is very high.

In the above mentioned case, the upper surface temperature $\theta_1$ of specimen S should be set slightly higher than measuring temperature T and the lower surface temperature $\theta_2$ should be set slightly lower than temperature T. The mean temperature of $\theta_1$ and $\theta_2$ is then considered to be the average internal temperature of specimen S and can be regarded as the measuring temperature T at which the measuring will be conducted. In other words, the values of $\theta_1$ and $\theta_2$ are each kept at a point which satisfies the following formula.

$$T = (\theta_1 + \theta_2)/2$$

The assumption that mean temperature of the upper and lower surfaces is the internal mean temperature of specimen S is valid as long as the thermal conductivity of specimen S is constant and its internal temperature changes rectilinearly between $\theta_1$ and $\theta_2$ as shown as B in FIG. 15.

However, in reality, the thermal conductivity of specimen S varies according to temperature. Therefore the internal temperature does not change rectilinearly, but makes a curvilinear change shown as "B'" in FIG. 16.

For large temperature differences between $\theta_1$ and $\theta_2$ there is a big difference between the internal mean temperature T, obtained by assuming the simple average of $\theta_1$ and $\theta_2$, and the actual internal mean temperature T. Thus the simple average temperature of the two surfaces does not represent the overall mean temperature of specimen S.

However, if the temperature difference between $\theta_1$ and $\theta_2$ is small, the change of temperature can be regarded as a rectilinear change and the difference between the two values of temperatures T and T' can be disregarded.

However, if the temperature difference is too small, other problems will arise. Decreasing the amount of temperature difference makes it necessary to reduce the thickness of specimen S. The decrease in temperature difference however makes it more difficult to maintain the temperature difference between the upper and lower surfaces of specimen S constant. Furthermore, temperature measurement errors will cause a magnification of the error in the results, when the temperature difference is very small. For these reasons, it is virtually always the case that a large temperature difference is employed according to the conventional thermal conductivity measuring apparatus.

SUMMARY OF THE INVENTION

The object of the present invention is to provide an accurate, easy method for measuring the thermal conductivity of a specimen at any desired temperature. According to the present invention, there is provided a method for measuring thermal conductivity, the method comprising the steps of:

(a) preparing a specimen of the material having first and second surfaces parallel to each other, thickness defined by the first and the second surfaces being constant, a sectional area parallel to the first and the second surfaces of the specimen being constant through the specimen;

(b) measuring heat flows Q1 to QN through the specimen at thermally stationary states S1 to SN wherein the temperature of the first surface of the specimen is To which is far lower than the temperature T and the temperature of the second surface of the specimen varies from a temperature T1 to a temperature TN, temperatures T1 and TN being in the vicinity of the temperature T and corresponding to the states S1 to SN; and (c) calculating the thermal conductivity of the specimen on its basis of the thickness and cross-sectional area, the temperatures of the first and the second surfaces, and the heat flow through the specimen.

DETAILED DESCRIPTION OF PREFERRED EMBODIMENTS OF THIS INVENTION

Embodiments of this invention will be described in detail referring to the figures.

The first preferred embodiment will be explained referring to FIGS. 1 to 4.

Figure 1:
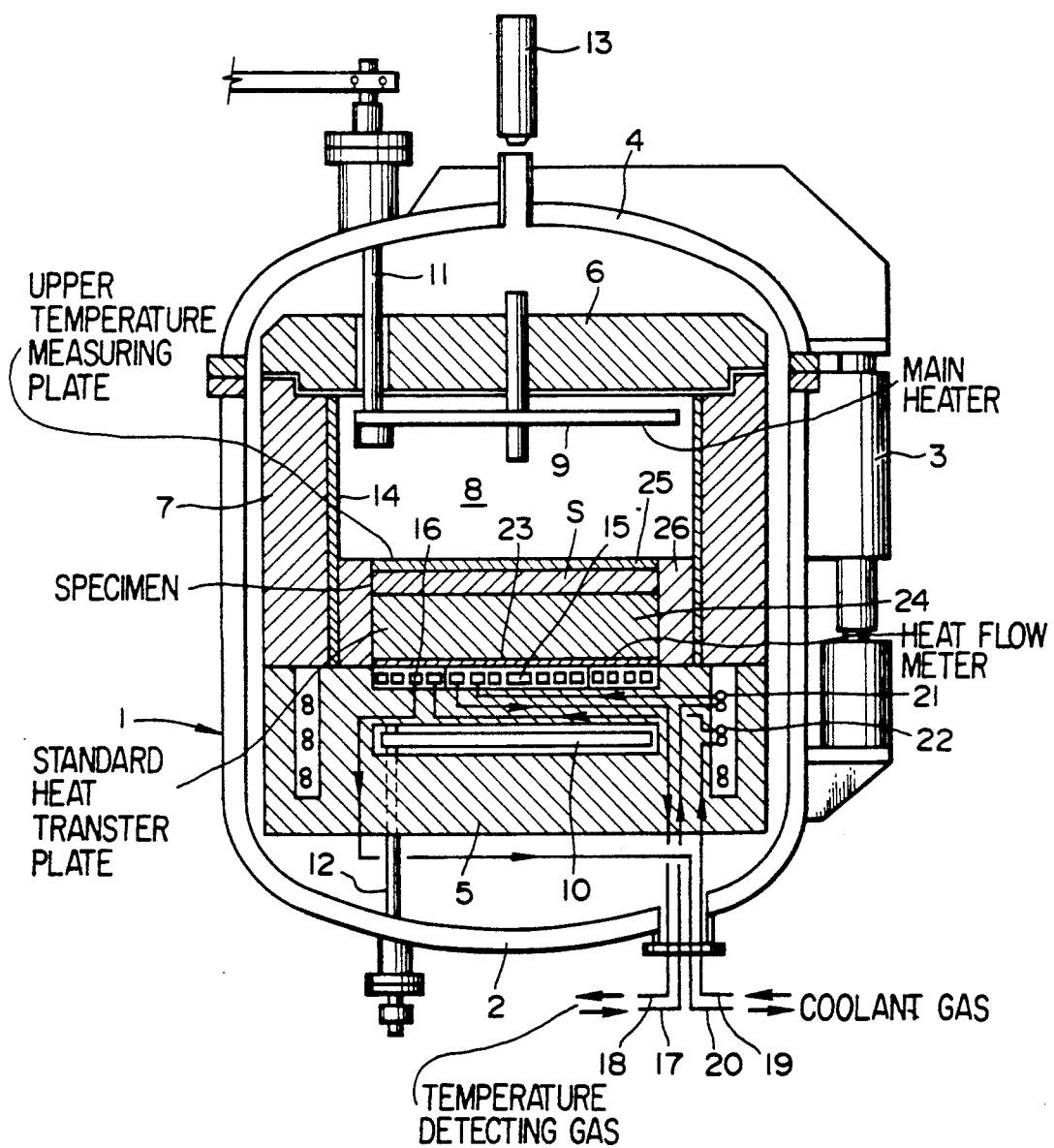
FIG. 1 is a vertical sectional view of a thermal conductivity measuring apparatus based on the first preferred embodiment of this invention.
Figure 2:
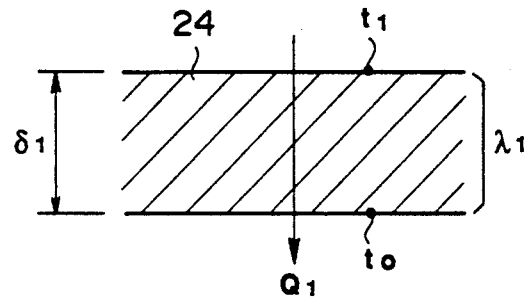
FIG. 2 is a schematic view which defines the parameters for measuring thermal conductivity of standard heat transfer plates.

FIG. 1 is a vertical sectional view of a thermal conductivity measuring apparatus which is appropriately used to illustrate the method of this embodiment. In this figure, housing 1 consists of a main body 2 and a cap 4 which is connected to the main body 2 with a hinge 3. The main body 2 has a water cooled jacket.

In the main body 2, measuring chamber 8 is defined by a lower heat insulator 5 and an upper heat insulator 6 and a cylindrical heat insulator 7. A main heater 9 is installed at the upper part of the measuring chamber 8 in order to keep the internal temperature of the chamber at a particular temperature.

In the lower heat insulator 5, an auxiliary heater 10 is embedded to keep the internal temperature of the lower heat insulator at the same temperature as the heat flow meter 15 (to be described later). Electric terminals 11 and 12, passing through the cap 4 and the main body 2, are connected to the main heater 9 and the auxiliary heater 10, respectively. A radiation type thermometer 13 is used to measure the internal temperature of the measuring chamber 8.

The internal surface of the cylindrical heat insulator 7, which forms the side walls of the measuring chamber 8, is coated with a heat compensating plate 14 which is made of a material wit sufficient heat resistance and high thermal conductivity, such as graphite, heat resistant steel or molybdenum.

Figure 15:
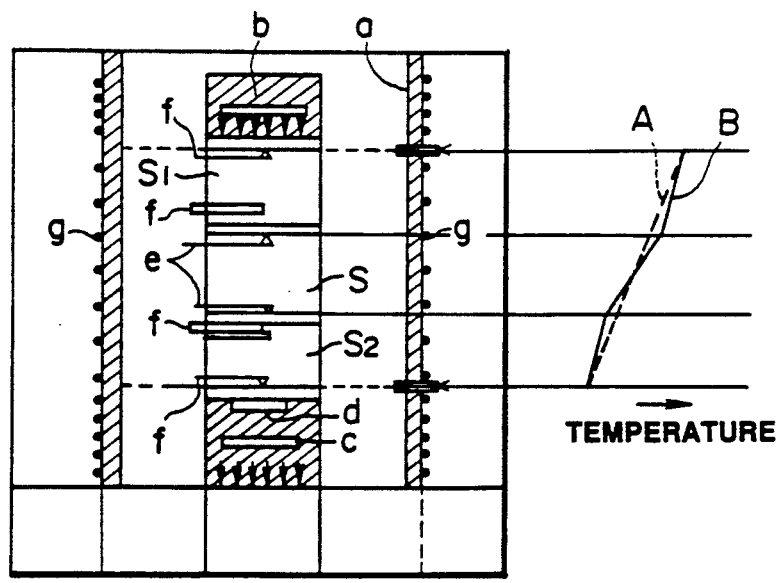
FIG. 15 is a vertical sectional view which shows a schematic structure of a conventional means of measuring thermal conductivity.

The high thermal conductivity of the heat compensating plate 14 allows the heat to flow downward from the chamber 8, maintaining a temperature distribution similar to that through the specimen S and also through the standard heat transfer plate 24. The internal temperature of the cylindrical heat insulator 7 can therefore be kept the same as that of specimen S or standard heat transfer plate 24 (described later). Moreover, a heater g which is used in a conventional measuring means (FIG. 15) for the purpose of temperature compensation of the side walls is not necessary, and thus the structure can be simplified and its size ca be reduced.

At the center of the lower heat insulator 5, a disc-shaped heat flow meter 15 is positioned with a ring-shaped auxiliary cooling plate 16 disposed around its periphery. A spiral passage is formed inside the heat flow meter 15 so as to measure the heat flow. A lead-in duct 17 and lead-out duct 18 are connected to the spiral passage to carry the temperature detecting gas flow to and from the spiral passage in the direction indicated by the arrow in the figure.

Inside the auxiliary cooling plate 16, a spiral passage, through which gas coolant runs, is formed. A lead-in duct 19 and a lead-out duct 20 are connected to the spiral passage so as to carry the coolant gas to and from the spiral passage in the direction indicated by the arrow in the figure.

The heat detecting gas and the coolant gas are heated to a certain temperature by gas pre-heaters 21 and 22 which are embedded at a lower part of the heat insulator 5 and then pass to the heat flow meter 15 and the auxiliary cooling plate 16 respectively.

Although they are not illustrated in the figure, thermometers are installed in order to measure the temperatures of the two gases at the spiral passage inlet and outlet.

Heat flow meter 15 is designed to enable the quantity of heat received by the heat detecting gas to be determined, that is, the heat flow through specimen S, from the temperature difference between the detecting gas temperature at the spiral inlet and outlet, and the flow rate of the gas. The auxiliary cooling plate 16 is placed around the heat flow meter 15 and kept at the same temperature as the heat flow meter so as to prevent heat transfer between the two.

Placed upon the upper surface of the said heat flow meter 15 and the auxiliary cooling plate 16 is the lower temperature measuring plate 23. Upon the upper surface of the lower temperature measuring plate 23, the standard heat transfer plate 24, which has heat insulating properties, is placed. The specimen S is placed upon the upper surface of the standard heat transfer plate 24 for measurement of its thermal conductivity. Upon the upper surface of the specimen, upper temperature measuring plate 25 is placed.

Thermocouples are located on the top face of the lower temperature measuring plate 23 and the lower face of the upper temperature measuring plate 25 (not illustrated in the figure). The lower surface temperature of the standard heat transfer plate 24 and the upper surface temperature of specimen S are measured with these thermocouples and the upper surface temperature of the upper temperature measuring plate 25 is measured with radiation thermometer 13. Element 26 in the figure is a thermal insulator.

Next is a description of a measuring method using this apparatus.

The measuring method, which will be discussed hereafter, is an indirect way in which thermal conductivity $\lambda_s$ of specimen S at temperature T° C. (Precisely, T° C. is the mean temperature which is determined from $(T+t_1')/2$ for cases where the difference between T and $t_1'$ is small), is obtained by a calculation using the measured average thermal conductivity $\delta_1$ of the standard heat transfer plate 24 without measuring the lower surface temperature of the specimen S.

Standard heat transfer plate 24 is placed on the upper surface of the lower heat flow meter 23. The upper temperature measuring plate 25 is then, directly placed upon the upper surface of the standard heat transfer plate 24 without this specimen S. The measuring chamber 8 is closed and hermetically sealed with the upper heat insulator 6 and the cap 4 of the housing 1.

Heat conductivity of the standard heat transfer plate 24 can then be measured according to the steps described below.

The main heater 9 and an auxiliary heater 10 are adjusted in order to generate a steady heat flow in the measuring chamber 8 in the same way as the conventional means. The heat detecting gas and the gas coolant are then warmed to a certain temperature by gas pre-heaters 21 and 22 respectively. The two respective gases are passed through the heat flow meter 15 and the auxiliary cooling plate 16 to maintain the temperature of those plates at the same temperature as that of the two gases. Once a steady state condition is established, the inlet and outlet temperatures and rate of flow of the heat detecting gas through the heat flow meter 15 are measured. From the temperature difference between the inlet and outlet temperatures, flow rate and gas properties, the rate of heat flow through standard heat transfer plate 24 can be obtained.

From the value of heat flow, and the upper surface temperature and the thickness of the standard heat transfer plate 24, the average thermal conductivity of the standard heat transfer plate 24 is determined by formula (2).

With the heat flow of the standard heat transfer plate 24 referred to as $Q_1$, the lower surface temperature of the plate as $t_0$, the upper surface temperature as $t_1$, the thickness of the plate as $\delta_1$, and the average thermal conductivity of the plate at this temperature as $\lambda_1$ the value of $\lambda_1$ can be obtained by the following formula which holds for the relationship among these factors.

$$Q_1 = (\lambda_1/\delta_1) A(t_1 - t_2) \qquad (2)$$

In this case, the effective area A of the standard heat transfer plate 24 is the area of the heat flow meter 15.

The next step is to keep the lower surface temperature $t_0$ at a certain temperature while the upper surface temperature $t_1$ is heated until it becomes higher that the measurement temperature T.

Figure 3:
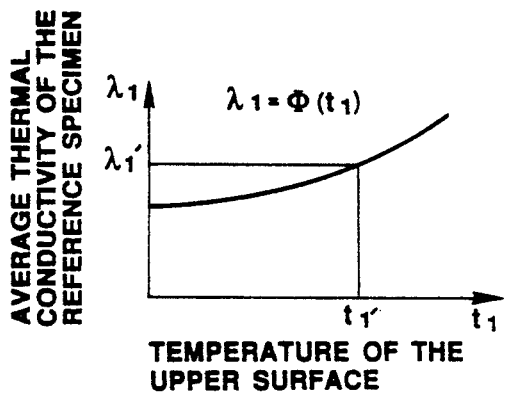
FIG. 3 shows the relationship between thermal conductivity and surface temperatures of standard heat transfer plates.

While increasing the temperature in steps, the average thermal conductivity of the plate is measured at each temperature step in the same manner as described above. Based upon the measurement result, a chart is drawn of the relationship between the average thermal conductivity $\lambda_1$ and the upper surface temperature $t_1$ as shown in FIG. 3 by changing the temperature of the specimen S in steps.

Since $\lambda_1$ is a function of $t_1$, it can be described as follows:

$$\lambda_1 = Q_t = \{\lambda_t/(\delta_1 + \delta_2)\} A(T - t_0)$$

$$Q_t = \phi(t_1) \qquad (3)$$

Function Ph can be determined approximately by computer processing of as much data as possible. This function differs depending upon the material of standard heat transfer plate 24.

After acquiring the values of $\lambda_1$ by means of equation (3) for different temperature (the temperatures are chosen so that they are grouped around the temperature T), specimen S is laid upon the upper surface of the standard heat transfer plate 24 and upper temperature measuring plate 25 is laid upon the upper surface of the specimen.

Figure 4:
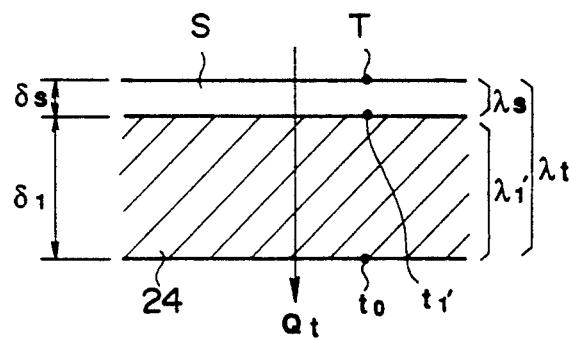
FIG. 4 defines the parameters for measuring thermal conductivity of a specimen laid on a standard heat transfer plate.

As illustrated in FIG. 4, the lower surface temperature of the standard heat transfer plate 24 is kept at temperature $t_0$ and the upper surface temperature of specimen S is kept at measuring temperature T. Once steady state conditions are established, the heat flow $Q_t$ is measured.

Provided that the thickness of a specimen is referred to as $\lambda_s$ and the integrated thermal conductivity of the specimen S and the standard heat transfer plate 24 are referred to as $\lambda_t$, then the following formula holds:

$$Q_t = \{\lambda_t/(\delta_1 + \delta_s)\} A(T - t_0) \qquad (4)$$

As a result of this formula, the integrated thermal conductivity $\lambda_t$ of specimen S and standard heat transfer plate 24 can be obtained.

Consider the state illustrated in FIG. 4 separately for specimen S and standard heat transfer plate 24, and assume that the thermal conductivity of specimen S is $\lambda_s$, the lower surface temperature of the specimen (which is equal to the upper surface temperature of the standard heat transfer plate 24) is $t_1'$, and the average thermal conductivity of the standard heat transfer plate is $\lambda_1'$, then from formula (4), because each of the two heat flows, one is through the specimen S and the other is through the standard heat transfer plate 24 is equal to the overall heat flow, the heat flow can be expressed as follows:

$$Q_t = \{\lambda_t/(\delta_1+\delta_s)\} A(T-t_0) \quad (4)$$

$$= (\lambda_1'/\delta_1) A(t_1'-t_0) \quad (4)'$$

$$= (\lambda_s/\delta_s) A(T-t_1') \quad (4)''$$

Thus the following will be obtained if Formula (4)' is equal to Formula (4)''.

$$(\lambda_1'/\lambda_1) A(t_1'-t_0) = (\lambda_s/\lambda_s) A(T-t_1') \quad (4)'''$$

On the other hand, the integrated heat resistance R of specimen S and standard heat transfer plate 24 in this condition can be represented as the sum of the heat resistance $R_1$ of standard heat transfer plate 24 and the heat resistance $R_S$ of specimen S; that is, $$R_t = (\delta_1+\delta_s)/A_t$$

$$R_1 = \delta_1/\lambda_1'$$

$$R_s = \delta_s/\lambda_s$$

Hence;

$$R_t = R_1 + R_s$$

Therefore, the following holds for the factors.

$$(\delta_1+\delta_s)/\lambda_t = (\delta_1'/\delta_1') + (\delta_s/\lambda_s) \quad (5)$$

In the above mentioned formulas, $\lambda_s$ is the final value for the thermal conductivity of specimen S at temperature T. More precisely, the thermal conductivity $\lambda_s$ corresponds to a state wherein the upper and the lower surfaces are T and $t_1'$ respectively.

Although $\lambda_1'$ and $t_1'$ are unknown values, the following relationship can be obtained because $\lambda_1'$ is the average thermal conductivity of the standard heat transfer plate 24 when the upper surface temperature is $t_1'$ and the lower surface temperature is $t_0$.

$$\lambda_1' = \phi(t_1') \quad (3)'$$

By solving simultaneous equations of formula (3)', (4)''' and (5), the three unknown values for $\lambda_s$, $\lambda_1'$, and $t_1'$ can be obtained. This calculation will be easily conducted with a microcomputer.

In spite of obtaining the value of Function $\phi$, it is also preferable to read the values of $\lambda_1'$ and $t_1'$, which satisfy the relations of formulas (4)''' and (5), from a chart showing the relationship between the average thermal conductivity $\lambda_1$ and the upper surface temperature $t_1$ such as in FIG. 3.

As described in the preceding paragraphs, with this first embodiment of this invention, the thermal conductivity $\lambda_s$ of specimen S can be obtained by calculation without measuring the lower surface temperature $t_1'$ of specimen S. It was difficult to measure the lower surface temperature of specimen S because it was laid directly upon the upper surface of standard heat transfer plate 24 in the conventional measuring means.

This measuring means can be appropriately applied for the measurement of thermal conductivity at very high temperatures in which case standard heat transfer plate 24 cannot be omitted.

In addition, the procedure for the means of measuring thermal conductivity can be simplified.

Precisely, the thermal conductivity $\lambda_s$ obtained by the above method is an average thermal conductivity at a state wherein the temperature of the upper and the lower surface of the specimen S is T° C. and t'° C. respectively. But, in the condition that T and t' are close to each other, the observation approximately gives a thermal conductivity at the temperature T° C.

If the same standard heat transfer plates are repeatedly used, then the average thermal conductivity is measured once at the beginning and a chart drawn similar to FIG. 3 in order to obtain the function $\phi$. This makes it unnecessary to measure the average thermal conductivity of the plates every time.

Figure 6:
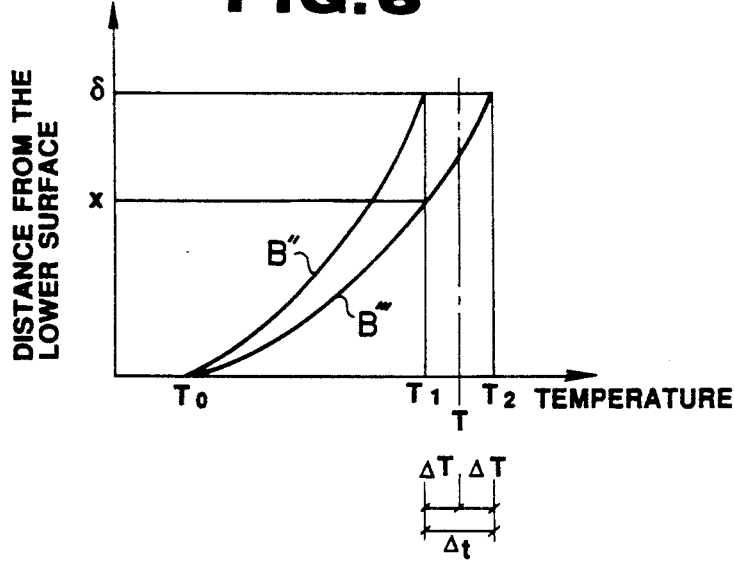
FIG. 6 shows the internal temperature distribution of a specimen based upon the second embodiment of this invention.
Figure 5:
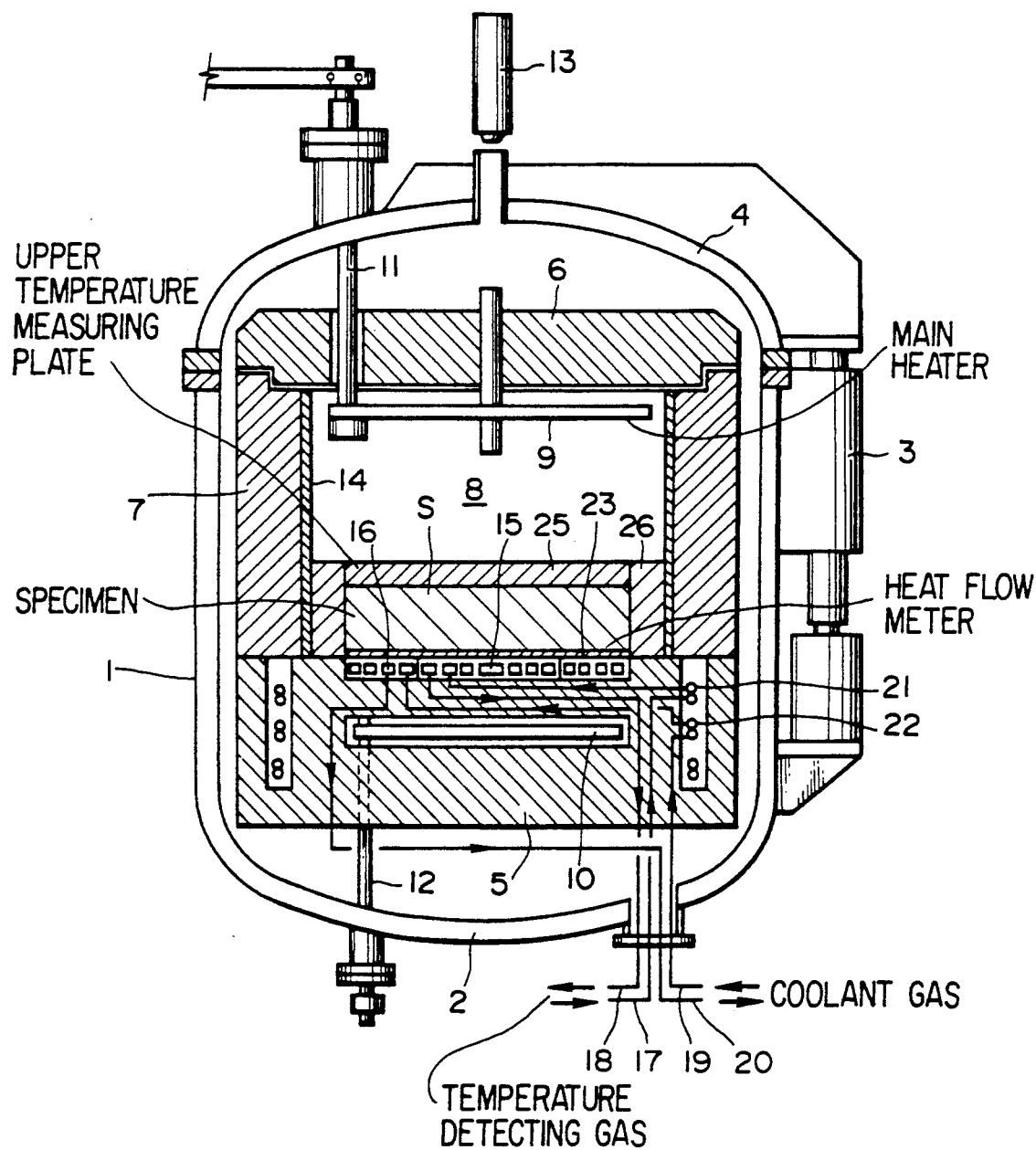
FIG. 5 is a vertical sectional view of a means for measuring thermal conductivity based on the second embodiment of this invention.

The following is a description of the second embodiment of this invention referring to FIGS. 5 and 6.

As shown in FIG. 5, a standard heat transfer plate, which is referred to as standard heat transfer plate 24 in the first embodiment, is omitted from this embodiment.

Upon the upper surface of lower temperature measuring plate 23, specimen S is directly placed. And the upper temperature measuring plate 25 is placed upon the upper surface of the specimen S.

This embodiment of the invention is designed to obtain the average thermal conductivity $\lambda$ of the specimen S at the measuring temperature T° C. wherein the temperature difference between the upper and lower surface of the specimen is supposed to be small, without using the standard heat transfer plate 24. The thermal conductivity $\lambda$ of the specimen S at T° C., in other words, is the thermal conductivity when the internal mean temperature of the specimen S is T° C.

In this case, the lower surface temperature of specimen S is kept at $T_0$ which is considerably lower than measuring temperature T and the upper surface temperature of specimen S is maintained at $T_1$ which is lower than T by $\Delta T$ (degrees). The value of $\Delta T$ should be as small as possible.

In the case where measurement temperature T is 2,000° C. for instance, the upper surface temperature $T_1$ is controlled to be as follows with the lower surface temperature $T_0$ at 100° C. and $\Delta T$ at 50 degrees.

$$T_1 = T - \Delta T = 1,950° C.$$

By this control, the temperature gradient is increased inside the specimen as indicated by B'' in FIG. 6. The average thermal conductivity $\lambda_{s1}$ of specimen S in this state will then be obtained.

Basically the heat measuring gas and coolant gas are heated up to a certain temperature by gas pre-heaters 21 and 22, in the same manner as with the first embodiment of this invention, and then led to heat flow meter 15 and auxiliary cooling plate 16 in order to keep them at the same temperature.

Once the internal temperatures of measuring chamber 8 and specimen S are at a steady state or no temperature change is detected (more specifically, if the temperature change over 10 minutes is constant within −0.5 and 0.5 degrees or within −0.1 and 0.1 percent of a certain allowable value), the inlet and outlet temperatures of the heat detecting gas are measured. From the difference of the temperatures and the flow rate, the heat flow through specimen S is obtained.

The average thermal conductivity $\lambda_{s1}$ of the specimen s in this state is obtained by formula (6) using the heat flow $Q_1$, the upper and lower surface temperatures of the specimen S and the thickness $\delta$ of the specimen S.

Incidentally, effective area A of the specimen S is the area of heat flow meter 15.

$$Q_1 = (\lambda_{s1}/\delta)A(T_1 - T_0) \quad (6)$$

$$T_1 = T - \Delta T$$

Thus, average thermal conductivity $\lambda_{s1}$, in the state in which the upper surface temperature is $T_1$ and the lower surface temperature is $T_0$, can be obtained.

The next step is to raise the upper surface temperature to $T_2$ which is higher than T by $\Delta T$ (in this example, $T_2 = 2,050°$ C.).

Once a steady state is established, heat flow $Q_2$ is measured in the same manner as mentioned before and thermal conductivity $\lambda_{s2}$ is obtained in this state from formula (7).

$$Q_2 = (\lambda_{s2}/\delta)A(T_2 - T_0) \quad (7)$$

$$T_2 = T + \Delta T$$

Thus, average thermal conductivity $\lambda_{s2}$, in the state in which the upper surface temperature is $T_2$ and the lower surface temperature is $T_0$, can be obtained.

The temperature gradient which is shown as B''' in FIG. 6 will increase in specimen S in this state.

Provided that the distance from this temperature gradient curve B''' to the part on the lower surface of specimen S (at which the internal temperature is $T_1$) is x, and the thickness of specimen S is divided into a part from the lower surface to x, and a part from x to the upper surface, formula (7) can be developed as follows: (Because heat flow $Q_2$ is the same in the two parts as long as they are in a steady state condition.)

$$Q_2 = (\lambda_{s2}/\delta)A(T_2 - T_0) \quad (7)$$

$$= (\lambda_{s1}/X)A(T_1 - T_0) \quad (7)'$$

$$= \{\lambda/(\delta - x)\}A(T_2 - T_1) \quad (7)'''$$

Formula (7)' represents the heat balance of the part from the lower surface of the specimen to x hereof. Since the upper surface temperature (the temperature at x) is $T_1$, and the lower surface temperature $T_0$, the value of average thermal conductivity obtained hereupon is $\lambda_{s1}$ which is obtained by formula (6).

Formula (7)''' represents the heat balance of the part from x to the upper surface of the specimen. Since the upper surface temperature is $T_2$ and the lower surface temperature (the temperature at x) is $T_1$, the value of thermal conductivity La is the final value for the thermal conductivity.

Provided that formula (7) = formula (7)', the following will be obtained.

$$X = (\lambda_{s1}/\lambda_{s2}) \cdot \delta \cdot (T_1 - T_0)/(T_2 - T_1) \quad (8)$$

Provided that formula (7)' = formula (7)'' substituting into formula (8) gives;

$$\lambda = \lambda_{s2} \cdot (T_2 - T_0)/(T_2 - T_1) - \lambda_{s1} \cdot (T_1 - T_0)/(T_2 - T_1) \quad (9)$$

$$T_2 - T_1 = 2\delta T = \delta t$$

$$T_1 = T_2 - \Delta t$$

On the other hand, if $T_2 - T_1 = 2 \Delta T = \Delta t$, then $T_1 = T_2 - \Delta/t$. Substituting them into formula (9), the following will be obtained.

$$\lambda = \lambda_{s2} \cdot (T_2 - T_0)/\Delta_t - \lambda_{s1} \cdot \{(T_2 - T_0) \Delta t - 1\} \quad (9)'$$

With formula (9) or (9)', average thermal conductivity $\lambda$ in the state in which the upper surface temperature is $T_2$ and the lower surface temperature is $T_1$, can be obtained.

There will be no problem if the simple mean temperature of $T_1$ and $T_2$ is regarded as the internal mean temperature of specimen S because the difference between $T_1$ and $T_2$ is sufficiently small.

Thus, the value of La which is obtained by formulas (9) and (9)' can considered to be the value of thermal conductivity at $T = (T_1 + T_2)/2$.

As described in the preceding paragraphs, in this second embodiment of the invention, average thermal conductivity $\lambda_{s1}$ is measured at upper surface temperature $T_1$, which is slightly lower than the measuring temperature and $\lambda_{s2}$ at $T_2$, which is slightly higher than the measuring temperature while the lower surface of the specimen is kept at $T_0$ which is considerably lower than the measuring temperature, From the values of $\lambda_{s1}$ and $\lambda_{s2}$, thermal conductivity $\lambda$ is calculated for measuring temperature T. Thus an accurate measurement of temperature can be achieved without use of the standard heat transfer plate 24 of the first embodiment. This accuracy of measurement makes it possible to obtain easily and precisely the value of thermal conductivity La at any desired measuring temperature T.

What is more, since actual measurement is carried out in such a state that a big difference between the upper and lower surface temperatures is ensured, the specimen temperature can be easily controlled and measurement errors can be minimized.

Figure 7:
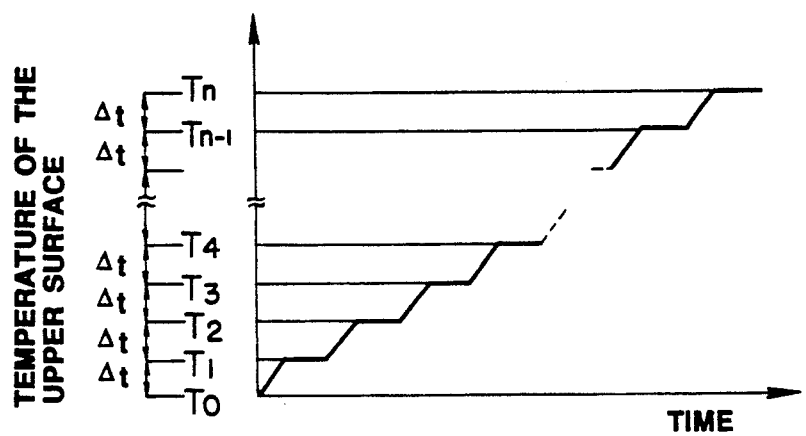
FIG. 7 shows the surface temperature of a specimen based upon the third embodiment of this invention.
Figure 8:
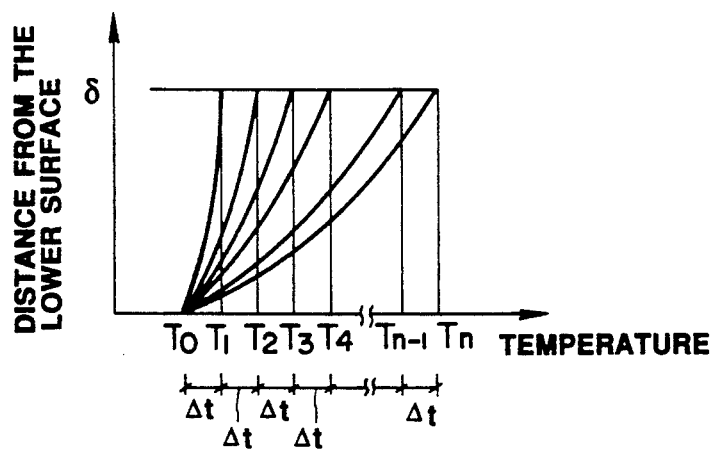
FIGS. 8 and 9 show the internal temperature distribution of a specimen based upon the third embodiment of this invention.
Figure 9:
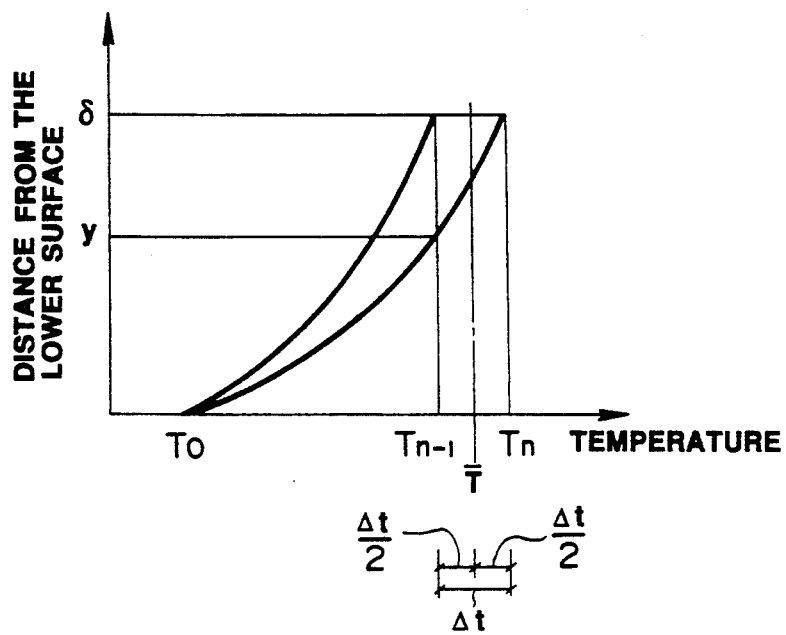

The next is a description of the third embodiment of this invention referring to FIGS. 7 to 9.

The measurement steps of this embodiment are designed to basically follow those of the second embodiment; namely, the upper surface temperature is increasingly raised by $\Delta t$ degrees from $T_0, T_1, T_2, \ldots$ up to $T_n = T_0 + N \Delta T$, whereas the lower surface temperature is kept at the same temperature $T_0$.

Under this control of temperature, temperature gradient will gradually rise inside specimen S as shown in FIG. 8.

In this case, the lower surface temperature of the specimen is $T_0$ and the upper surface temperature is $T_{n-1} = T_0 + (N-1) \Delta t$ at (N−1)th measurement as shown in FIG. 9. Thus the difference between $T_0$ and $T_{n-1}$ is $(N-1)\Delta$. Provided that the heat flow is designated as $Q_{n-1}$ and the average thermal conductivity as $\lambda_{n-3}$ 1 1, the following formula will hold for $Q_{n-1}$ and $\lambda_{n-1}$:

$$Q_{n-1} = (\lambda_{n-1}/\lambda) A \cdot (N-1) \Delta t \qquad (10)$$

Since the lower surface temperature remains $T_{0S}$ and the upper surface temperature is $T_n = T_0 + N \Delta t$ at the n-th measurement, the difference of the two temperatures will be $N \Delta t$. Provided that the heat flow is designated as $Q_n$ and the average thermal conductivity as $\lambda_n$, the following formula will hold for the two.

$$Q_n = (\lambda_n/\lambda) A \cdot N \Delta t \qquad (11)$$

In the state of the n-th measurement, should the distance (from the lower surface to a part where the internal temperature of a specimen is the same as the previous temperature $T_{n-1}$) be designated as y and the thickness of a specimen be divided into two parts, namely one from the lower surface to y and the other from y to the upper surface, then formula (11) can be developed in the same way as formulas (7)' and (7)''

$$Q_n = (\lambda_n/\lambda) A \cdot N \Delta t \qquad (11)$$

$$= (\lambda_{n-1}/y) A \cdot (N-1) \Delta t \qquad (11)'$$

$$= \{\Lambda_n/(\delta - y)\} A \cdot \Delta t \qquad (11)''$$

$\Lambda_n$ means that the upper surface temperature is $T_n = T_0 + N \Delta t$ and the lower surface temperature (which is the temperature at y) is $T = T_0 + (N-1) \Delta t$. Thus the thermal conductivity, with the temperature difference $\Delta t$ and the simple means temperature is $\overline{T}_n = (T_{n-1} + T_n)/2$, is the final value to be obtained.

Solving the above mentioned formulas, the following will be obtained.

$$y = (\lambda_n/\lambda_{n-1})(1 - 1/n) \delta \qquad (12)$$

Hence, $$\Lambda_n = N \cdot \lambda_n - (N-1) \cdot \lambda_{n-1} \qquad (13)$$

In other words, the average thermal conductivity, while the upper surface temperature is $T_n$s and the lower surface temperature $T_{n-1}$, will be obtained from the measurement results $\lambda_n$ of the n-th measurement and $\lambda_{n-1}$ of the (N−1)th measurement.

In addition, the following formulas can be established.

$$\overline{T}_n = (T_{n-1} + T_n)/2$$

$$= T_{n-1} + \Delta t/2$$

$$= T_n - \Delta t/2$$

The value of $\overline{T}_n$ can be regarded as the internal mean temperature of a specimen by reducing $\Delta t$ or by reducing the difference between $T_{n-1}$ and $T_n$.

Figure 14:
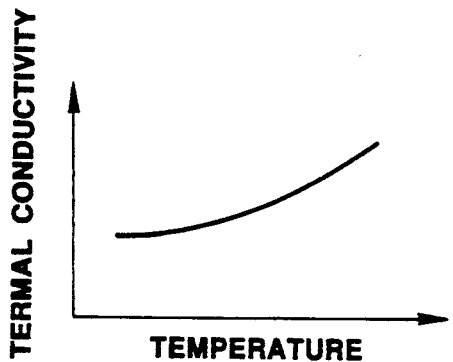
FIG. 14 shows the relationship between thermal conductivity and temperatures of various materials.
Figure 16:
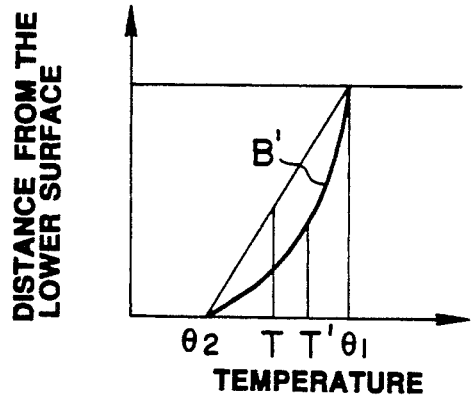
FIG. 16 shows an internal thermal state of a specimen when the thermal conductivity of the specimen is being measured.

With this measurement method of the third embodiment, thermal conductivity of a specimen at various temperatures can be easily obtained. By minimizing the value of $\Delta t$, a continuous graph as shown in FIG. 14 can be created to show the relationship between thermal conductivity and temperatures.

Just as in the second embodiment (since actual measurement is conducted by setting lower surface temperature $T_0$ of a specimen at a sufficiently low temperature and maintaining a large temperature differential) it is easy to maintain the temperature of a specimen thus measurement errors will be reduced.

In the following paragraphs, a fourth embodiment of this invention will be described referring to FIG. 10.

As for obtaining the thermal conductivity $\lambda$ of specimen S at calculation temperature T° C., this method of the fourth embodiment also keeps the lower surface temperature of specimen S at $T^o$ which is considerably lower than calculation temperature T in the second and third embodiments. On the other hand, upper surface temperature $T_m$ of specimen S is set substantially higher than lower surface temperature $T_0$ and measured at least three times. Applying formula (9) which was introduced in the second embodiment, this method is designed to obtain the thermal conductivity La at calculation temperature T by calculation.

When the lower surface temperature of specimen S is designated as $T_0$, and the upper surface temperature $T_m$ is set at a desired temperature $T_{ml}$, the heat flow $Q_{ml}$ is measured in that state and the average thermal conductivity $\lambda_{ml}$ can then be determined based on the value of $Q_{ml}$ and by the following formula:

$$Q_{ml} = (\lambda_{ml}/\lambda) A (T_m - T_0) \qquad (14)$$

The upper surface temperature $T_m$ is then changed to a desired temperature $T_{m2}$ while the lower surface temperature is maintained at $T_0$. Then heat flow $Q_{m2}$ is measured in that state and average thermal conductivity $\lambda_{m2}$ can be obtained by the following formula as described in the preceding paragraph.

$$Q_{m2} = (\lambda_{m2}/\lambda) A (T_{m2} - T_0) \qquad (14)'$$

The upper surface temperature $T_m$ is then changed to a desired temperature $T_{m1}$ through $T_{m3}$ while the lower surface temperature is maintained at $T_0$. $T_{m1}$ through $T_{m3}$ are determined so as to be sufficient to plot the graph shown in FIG. 10. Then the heat flow $Q_{m3}$ is measured and the average thermal conductivity $\lambda_{m3}$ is obtained by the following formula.

$$Q_{m3} = (\lambda_{m3}/\delta) A (T_{m3} - T_0) \qquad (14)''$$

Figure 10:
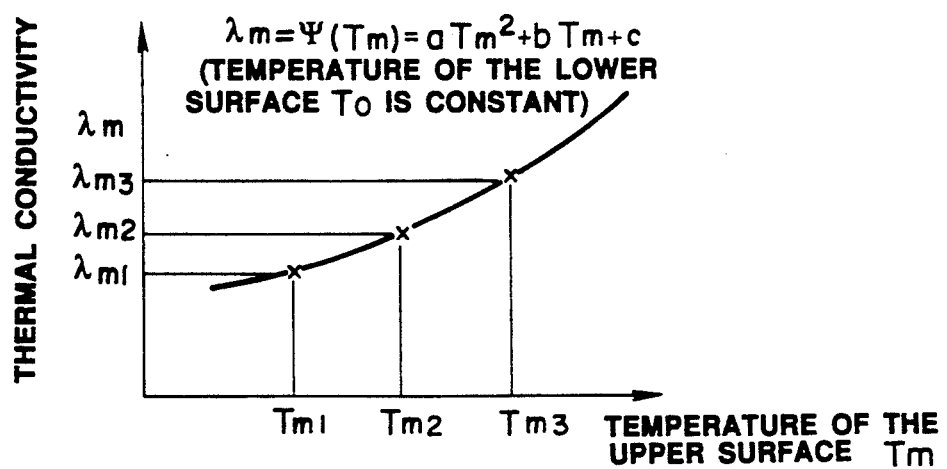
FIG. 10 shows a functional relationship between the upper surface temperature and thermal conductivity of a specimen.
Figure 11:
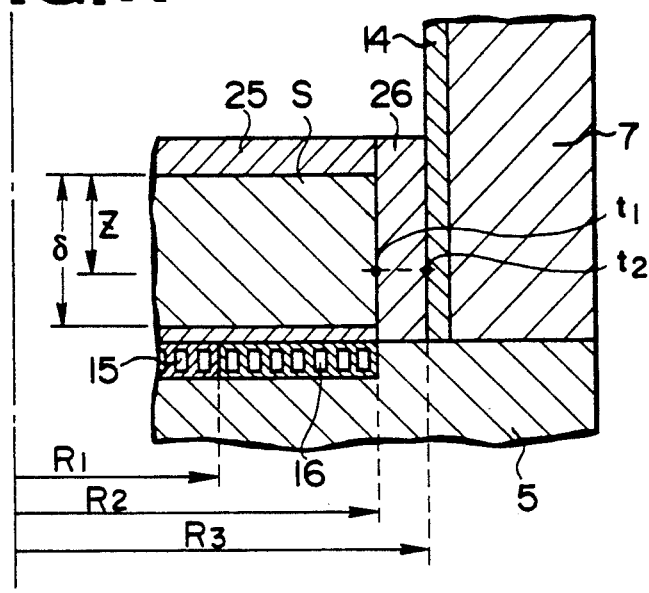
FIG. 11 is a view used to explain the correction of measurement errors which arise due to radial heat flow in the above mentioned embodiments of this invention.

The three different temperatures of the upper surface of the specimen $T_{m1}$, $T_{m2}$ and $T_{m3}$ should be set considerably higher than the lower surface temperature $T_0$, for example, at an appropriate temperature such that the graph described in FIG. 10 can be applied near the calculation temperature T. Likewise, the differences among them can be freely chosen.

Based upon the measurement results obtained as described above, a graph is drawn with the upper surface temperature of specimen S as abscissa, and average thermal conductivity $\lambda_m$ as ordinate, and a quadratic function which represents the relationship between and $\lambda_m f$ and $T_m$.

$$\lambda_m = \Psi(T_m) = aTm^2 + bTm + c \qquad (15)$$

For this formula, the values of a, b, and c are determined by the least squares approximation method.

Once function $\Psi$ is determined, when the lower surface temperature is set at $T_o$ and the upper surface temperature $T_n$ is variable, the average thermal conductivity can be obtained by formula (15) or read from FIG. 10.

In the case where the lower surface temperature is $T_0$ and the upper surface temperature is $T_1$, the average thermal conductivity $\lambda_{s1}$ is thus obtained by formula (16).

$$\lambda_{s1} = aT_1^2 + bT_1 + c \qquad (16)$$

The average thermal conductivity $\lambda_{s2}$ with lower surface temperature $T_0$ and upper surface temperature $T_2$ is obtained by the following formula.

$$\lambda_{s2} = aT_2^2 + Bt_2 + c \qquad (17)$$

Substituting the values of $\lambda_{s1}$ and $\lambda_{s2}$ into formula (9), which is used to obtain thermal conductivity $\lambda$, in the case where the lower surface temperature is $T_1$, and the upper surface temperature is $T_2$, the following formula can be obtained:

$$\lambda = a(T2^2 + T2T1 + T1^2) + (b - aT_0)(T2 + T1) + (c - bT_0) \qquad (18)$$

By this formula, the thermal conductivity $\lambda$ where the lower surface temperature is $T_1$, and the upper surface temperature is $T_2$ (in which case the internal mean temperature of specimen S is the calculation temperature T), can be calculated from only the values of $T_1$ and $T_2$, the values of a, b and c in function $\Psi$ of formula (15), and the value of lower surface temperature $T_0$ of specimen S obtained during the measurement for determining the function $\Psi$.

Once function $\Psi$ is determined, it will not be necessary to measure the upper surface temperature near calculation temperature T. The value of the thermal conductivity $\lambda$ at the calculation temperature T can be calculated by formula (18).

The value of thermal conductivity $\lambda$, the final goal of this measuring method, is the value when the difference between $T_1$ and $T_2$ is infinitely small; that is, in the case where $T_2$ is nearly equal to $T_1 = T$. By substituting $T_2 = T_1 = T$ into formula (18), the following formula can be obtained:

$$\lambda = 3aT^2 + 2(b - aT_0) T + (c - bT_0) \qquad (19)$$

By this formula (19), the thermal conductivity $\lambda$ of specimen S at calculation temperature T can be obtained.

A subsequent calculation of $\lambda$ at any desired temperature T can be carried out by formula (19). Since a graph similar to FIG. 14 can be easily drawn from the formula, the thermal conductivity $\lambda$ at the desired calculation temperature T can be read from the graph.

As described in the preceding paragraphs with the measuring method of this embodiment, thermal conductivity is measured three times by changing the upper surface temperature $T_m$ while keeping the lower surface temperature at the same temperature $T_0$. Based upon the results of the three measurements, function $\Psi$, which represents the relationship between the upper surface temperature T and thermal conductivity $\lambda$ can be determined. The thermal conductivity $\lambda$ at a desired calculation temperature T can finally be calculated based upon the determined function $\Psi$. Thus the value of thermal conductivity $\lambda$ at any desired calculation temperature T can be easily and accurately obtained.

Because the measurement is required to be done only three times in order to determine function $\Psi$, temperature control of specimen S is easy and measuring errors are limited as much as possible since the three measurements are conducted with a large temperature difference maintained between the upper and lower surfaces.

The function in the fourth embodiment is a quadratic function and the thermal conductivity measurement is carried out three times. However, it is not limited to a quadratic. Any type of function, a function of higher degrees or an exponential function, for instance, can be applied as long as it accurately represents the measurement results. If another type of function is applied, then measurement of thermal conductivity should be done as many times as necessary to precisely determine function $\Psi$.

Descriptions of the embodiments of this invention are now finished.

Each step in the measuring procedures of the embodiments can be conducted manually. However, it is highly recommended to equip the measuring means of thermal conductivity with a microcomputer and to program in advance all steps of the measurement to an electronic device so that all procedures of control and calculation of average thermal conductivity from measurement values ca be immediately processed by the microcomputer.

It should be noted that heat may flow from the side part of specimen S through heat insulator 26 (see FIGS. 1 and 5) when conducting measurement through the above described procedures with the said measuring means of thermal conductivity and that this heat flow may create measurement errors. In order to carry out more accurate measurement, the radial flow quantity is determined by measuring the internal and external temperatures of heat insulator 26 then the measured value of heat flow which is obtained by the heat flow meter 15 is corrected.

When the internal mean temperature of heat insulator 26 is designated as $t_1$, the external mean temperature of the heat insulator as $t_2$, the thermal conductivity of the heat insulator as $\lambda b$, the inside diameter as $R_2$, the outer diameter as $R_3$, and the thickness of specimen S as $\delta$, heat quantity $Qb$ which affects the area of specimen S within effective diameter $R_1$ as heat flow from the side part of specimen S through heat insulator 26, will be represented as follows:

$$Qb = \{\lambda b/(R_3 - R_2)\}(R_1 R_2)^4 \cdot 2\pi Rm\delta(t_1 - t2)$$

However, $$Rm = (R_3 - R_2) \ln(R_3/R_2)$$

Thus the value of Qb should be corrected in accordance with the value of the heat flow which is obtained by the heat flow meter 15.

Since the internal and external temperatures of heat insulator 26 are not uniform in the direction of the thickness of specimen S, it is preferable to measure the internal and external temperatures at points located at ⅓ or ⅔ of the thickness of specimen S ($z = (⅓\ ⅔)\ \delta$) from the upper surface of the specimen and to designate the temperatures as internal mean temperature $t_1$, and external mean temperature $t_2$ so as to represent the overall temperature of heat insulator 26.

Figure 12:
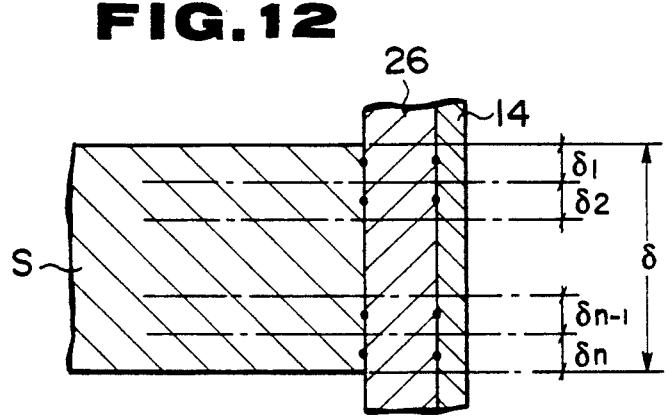
FIG. 12 is a enlarged view of a part of FIG. 11.

To be more exact, as shown in FIG. 12, it is recommended to divide heat insulator 26 into several parts with thicknesses of $\delta_1, \delta_2, \ldots, \delta_n$ and to measure the internal and external temperatures of each part. Based upon these temperatures, $Qb'$ can be obtained.

Provided that the internal temperature of each part is designated as $t_{1n}$ and the external temperature as $t_{2n}$, then Qb' will be represented as follows:

$$Qb = \{\lambda b/(3-R_2)\}(R_1/R_2)^4 \cdot 2\pi Rm(\pi\delta_n(t_{1n}-t_{2n}))$$

However, $$Rm = (R_3-R_2)/\ln(R_3/R_2)$$

Another possible reason for measurement errors is heat transfer which arises between heat flow meter 15 and auxiliary heater 10 due to the temperature difference between the two.

For the purpose of preventing these errors, it is preferable to measure the inlet and outlet temperatures of the heat detecting gas to and from the heat flow meter 15, in order to adjust the mean temperature of the inlet and outlet temperatures to become the same as that of the auxiliary heater 10. With this procedure, the heat transfer may be prevented or the following correction can be applied.

Figure 13:
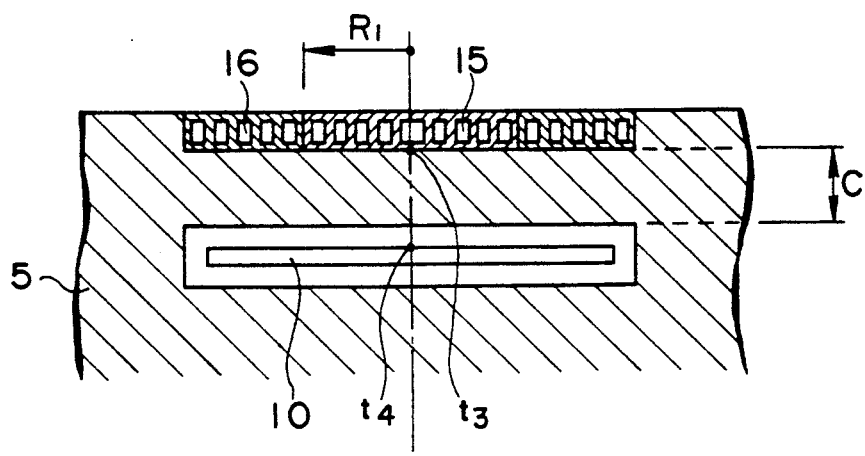
FIG. 13 is a view used to explain the correction of measurement errors which arise due to heat transfer between heat flow meters and the auxiliary heater.

As shown in FIG. 13, the quantity of heat transfer Qc between heat flow meter 15 and auxiliary heater 10 will be as follows, providing the thermal conductivity of heat insulator 5 is $\lambda c$, the thickness of the heat insulator is C, the diameter of the heat flow meter 15 is $R_1$, the lower surface temperature of the heat flow meter is $t_3$, and the surface temperature of auxiliary heater 10 is $t_4$.

$$Qc = (\lambda_c/C)\pi R_1^2(t_3-t_4)$$

For the correction, calculate Qc by measuring $t_3$ and $t_4$, then correct the value of Qc in accordance with the heat flow quantity which is obtained by the heat flow meter 15.

Furthermore, lower surface temperature $T_0$ of specimen S is always maintained at a fixed temperature regardless of the upper surface temperature. For this purpose, the quantity of heat detecting gas led into heat flow meter 15 should be adjustable. Thus the gas flow quantity can be controlled so as not to allow the temperature of heat detecting gas to increase excessively due to heat reception from specimen S.

The temperature rise should be limited within 5 to 10 degrees because minimum measurement errors arise within that range.

In the above preferred embodiments, the coolant to circulate through the heat flow meter was a gas. However any fluid such as water or oil may be employed instead of the gas.

What is claimed is:

1. A method of heating a specimen to determine its thermal conductivity comprising the steps of:
   (a) preparing the specimen to have first and second surfaces parallel to each other, a constant thickness defined by the first and second surfaces, and a constant cross-sectional area parallel to the first and the second surfaces;
   (b) introducing the prepared specimen into a heating chamber having an openable closure;
   (c) supplying heat within said chamber so as to heat said second surface to a temperature $T_i$;
   (d) carrying heat away from said first surface with a heat carrying medium while heat is supplied to said second surface so as to maintain said first surface at a temperature $T_o$;
   (e) stabilizing said specimen at a stationary state $S_i$ wherein said first surface has a temperature $T_o$ and said second surface has a temperature $T_i$;
   (f) measuring the flow of heat $Q_i$ being carried away from said first surface by said heat carrying medium necessary to maintain said specimen at said stationary state $S_i$;
   (g) repeating steps (c)–(f) N times and determining at each repetition of steps (c)–(f) a heat flow value to obtain respective heat flow values $Q_1$ to $Q_N$ for stationary states $S_1$ to $S_N$ of the specimen; and
   (h) determining the thermal conductivity of the specimen on the basis of said thickness and said cross-sectional area, the temperatures of the first and second surfaces, and the heat flows though the specimen;
   wherein the heat carrying medium is a fluid.

2. A method of heating a specimen to determine its thermal conductivity as recited in claim 1, wherein the fluid is at least one selected from the group consisting of: water, an oil, air and an inert gas.

3. A method of heating a specimen to determine its thermal conductivity, comprising the steps of:
   (a) preparing the specimen to have first and second surfaces parallel to each other, a constant thickness defined by the first and second surfaces, and a constant cross-sectional area parallel to the first and the second surfaces;
   (b) introducing the prepared specimen into a heating chamber having an openable closure;
   (c) supplying heat within said chamber so as to heat said second surface to a temperature $T_i$;
   (d) carrying heat away from said first surface with a heat carrying medium while heat is supplied to said second surface so as to maintain said first surface at a temperature $T_o$;
   (e) stabilizing said specimen at a stationary state $S_i$ wherein said first surface has a temperature $T_o$ and said second surface has temperature $T_i$;
   (f) measuring the flow of heat $Q_i$ being carried away from said first surface by said heat carrying medium necessary to maintain said specimen at said stationary state $S_i$;
   (f) repeating steps (c)–(f) N times and determining at each repetition of steps (c)–(f) a heat flow value to obtain respective heat flow values $Q_1$ to $Q_N$ for stationary states $S_1$ to $S_N$ of the specimen; and
   (h) determining the thermal conductivity of the specimen on the basis of said thickness and said cross-sectional area, the temperatures of the first and second surfaces, and the heat flows through the specimen;
   wherein said step of carrying heat away with a heat carrying medium comprises the substep of;
   forcing a heat flow detecting gas through a heat flow meter provided in contact with the said first surface of said specimen, and measuring a temperature difference of said heat flow detecting gas and a flow rate of said heat flow detecting gas.

4. A method of heating a specimen according to claim 3, further comprising the step of:
   pre-heating said heat flow detecting gas to a certain temperature before forcing said heat flow detecting gas through said flow meter.

5. A method of heating a specimen according to claim 4, wherein the heat flow detecting gas is a gas selected from the group consisting of: air and an inert gas.

6. A method of heating a specimen according to claim 3 wherein said step of measuring the flow of heat $Q_i$ comprises the substep of:

heating said heat flow detecting gas to a certain temperature;

forcing said heat flow detecting gas through a passage in said heat flow meter at a given flow rate;

allowing an input temperature and an output temperature of said heat flow detecting gas to stabilize; and determining said heat flow $Q_i$ from said output temperature, said input temperature, and said flow rate.

7. A method of heating a specimen to determine its thermal conductivity, comprising the steps of:

(a) preparing the specimen to have first and second surfaces parallel to each other, a constant thickness defined by the first and second surfaces, and a constant cross-sectional area parallel to the first and the second surfaces;

(b) introducing the prepared specimen into a heating chamber having an openable closure;

(c) closing and sealing said chamber;

(d) supplying heat within said chamber so as to heat said second surface to a temperature $T_1$, said temperature $T_1$ being lower than the temperature T by an amount $\Delta T$;

(e) carrying heat away from said first surface with a heat carrying medium while heat is supplied to said second surface so as to maintain said first surface at a temperature $T_o$, $T_o$ being lower than the temperature T by an amount many times $\Delta T$;

(f) stabilizing said specimen at a stationary state $S_1$ wherein said first surface is at temperature $T_o$ and said second surface is at said temperature $T_1$;

(g) measuring the flow of heat $Q_1$ being carried away from said first surface by said heat carrying medium necessary to maintain said specimen at said stationary state $S_1$;

(h) supplying additional heat within said chamber so as to heat said second surface to a temperature $T_2$, said temperature $T_2$ being higher than the temperature T by an amount $\Delta T$;

(i) stabilizing said specimen at a stationary state $S_2$ wherein said first surface is at temperature $T_o$ and said second surface is at temperature $T_2$;

(j) measuring the flow of heat $Q_2$ being carried away from said first surface by said heat carrying medium necessary to maintain said specimen at said stationary state $S_2$; and (k) determining the thermal conductivity $\lambda$ of the specimen according to the equation:

$$\lambda = \lambda_2 \cdot (T_2 - T_0)/(T_2 - T_1) - \lambda_1 \cdot (T_1 - T_0)/(T_2 - T_1)$$

by using a first average thermal conductivity $\lambda_1$ at the temperature $T_1$ and a second average thermal conductivity $\lambda_2$ at the temperature $T_2$;

wherein said step of carrying heat away with a heat carrying medium comprises the substep of:

forcing a heat flow detecting gas through a heat flow meter provided in contact with said first surface of said specimen, and measuring a temperature difference of said heat flow detecting gas and a flow rate of aid heat flow detecting gas.

8. A method of heating a specimen according to claim 7, wherein the heat carrying medium is a fluid.

9. A method of heating a specimen according to claim 8, wherein the fluid is at least one selected from the group consisting of: water, an oil, air, and an inert gas.

10. A method of heating a specimen to determine its thermal conductivity at a stationary state at a temperature T, comprising the steps of:

(a) preparing the specimen to have first and second surfaces parallel to each other, a constant thickness defined by the first and second surfaces, and a constant cross-sectional area parallel to the first and the second surfaces;

(b) preparing a reference plate to have first and second surfaces parallel to each other with substantially equal surface areas, a thickness defined by the first and the second surfaces being constant throughout the reference plate, a cross-sectional area parallel to the first and the second surfaces of the reference plate being constant throughout the reference plate, and the reference plate having a known thermal conductivity;

(c) introducing said reference plate into a measuring chamber having an openable closure;

(d) introducing the specimen into said measuring chamber such that said first surface of said specimen is in contact with said second surface of said reference plate;

(e) closing and sealing said openable closure of said measuring chamber;

(f) supplying heat within said chamber so as to heat said second surface of said specimen to a temperature higher than said temperature T;

(g) carrying heat away from said first surface of said reference plate with a heat carrying medium while heat is supplied to said second surface of said specimen, thereby maintaining said first surface of said reference plate at a temperature $T_o$, $T_o$ being far lower than the temperature T;

(h) stabilizing a temperature condition of said specimen and said reference plate at a stationary state $S_1$ with said first surface of said reference plate at said temperature $T_o$ and said second surface of said specimen constant at said temperature higher than temperature T;

(i) determining an integrated thermal conductivity of the specimen and the reference plate;

(j) measuring an integrated heat flow carried from said first surface of said reference plate by said heat carrying medium necessary to maintain said specimen and said reference plate at said stationary state $S_1$;

(k) estimating functional formulae respectively showing a relation between the thickness and cross-sectional area of the specimen and the reference plate, temperatures of the first surface of the reference plate, the temperature $T_o$, the temperature of the second surface of the specimen, the integrated heat flow through the specimen and the reference plate, the integrated thermal conductivity, and the thermal conductivity of the referee plate at the temperature T; and (l) determining the thermal conductivity of the specimen by solving simultaneously said functional formulae;

wherein said step of carrying heat away with a heat carrying medium comprises the substep of:

forcing a heat flow detecting gas through a heat flow meter provided in contact with said first surface of said specimen, and measuring a temperature difference of said heat flow detecting gas and a flow rate of said heat flow detecting gas.

11. A method of heating a specimen according to claim 10, wherein the reference plate and the specimen each have a thermal resistance, the thermal resistance of the reference plate being larger than the thermal resistance of the specimen.

12. A method of heating a specimen to determine its thermal conductivity at a stationary state at a temperature T, comprising the steps of:
    (a) preparing the specimen to have first and second surfaces parallel to each other, a constant thickness defined by the first and second surfaces, and a constant cross-sectional area parallel to the first and the second surfaces;
    (b) introducing the prepared specimen into a heating chamber having an openable closure;
    (c) supplying heat within said chamber so as to heat said second surface to a temperature $T_1$;
    (d) carrying heat away from said first surface with a heat carrying medium while heat is supplied to said second surface so as to maintain said first surface at a temperature $T_o$, $T_o$ being far lower than the temperature T;
    (e) stabilizing said specimen at a stationary state $S_1$ wherein said first surface is at temperature $T_o$ and said second surface is at said temperature $T_1$;
    (f) measuring the flow of heat $Q_1$ being carried away from said first surface by said heat carrying medium necessary to maintain said specimen at said stationary state $S_1$;
    (g) supplying additional heat when said chamber so as to heat said second surface to a temperature $T_2$;
    (h) stabilizing said specimen at a stationary state $S_2$ wherein said first surface is at temperature $T_o$ and said second surface is at temperature $T_2$;
    (i) measuring the flow of heat $Q_2$ carried away from said first surface by said heat carrying medium necessary to maintain said specimen at said stationary state $S_2$;
    (j) supplying additional heat within said chamber so as to heat said second surface to a temperature $T_3$;
    (k) stabilizing said specimen at a stationary state $S_3$ wherein said first surface is at temperature $T_o$ and said second surface is at temperature $T_3$;
    (l) measuring the flow of heat $Q_3$ being carried away from said first surface by said heat carrying medium necessary to maintain said specimen at said stationary state $S_3$;
    (m) estimating a function showing the relation between the thermal conductivity and the temperature of the specimen based on the thickness and cross-sectional area, temperature of the first and the second surfaces, and heat flows through the specimen, by supposing that the function is of second order; and
    (n) determining the thermal conductivity of the specimen at the predetermined temperature T using the function estimated in step (m) above;
wherein said step of carrying heat away with a heat carrying medium comprises the substep of:
    forcing a heat flow detecting gas through a heat flow meter provided in contact with said first surface of said specimen, and measuring a temperature difference of said heat flow detecting gas and a flow rate of said heat flow detecting gas.

13. A method of heating a specimen according to claim 12, wherein the heat carrying medium is a fluid.

14. A method of heating a specimen according to claim 13, wherein the fluid is at least one selected from the group consisting of: water, an oil, air, and an inert gas.

* * * * *